(12) United States Patent
Wilkinson

(10) Patent No.: US 9,861,784 B2
(45) Date of Patent: Jan. 9, 2018

(54) BLOOD COLLECTION DEVICE WITH DOUBLE PIVOT SHIELDS

(71) Applicant: Becton, Dickinson and Company, Franklin Lakes, NJ (US)

(72) Inventor: Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 512 days.

(21) Appl. No.: 14/095,383

(22) Filed: Dec. 3, 2013

(65) Prior Publication Data

US 2015/0151054 A1    Jun. 4, 2015

(51) Int. Cl.
*A61M 5/32* (2006.01)
*A61M 25/00* (2006.01)
*A61M 25/06* (2006.01)

(52) U.S. Cl.
CPC .... *A61M 25/0097* (2013.01); *A61M 25/0612* (2013.01); *A61M 5/3216* (2013.01); *A61M 2005/3217* (2013.01)

(58) Field of Classification Search
CPC .. A61M 5/3202; A61M 5/321; A61M 5/3216; A61M 5/3219; A61M 2005/3217; A61M 25/0612
See application file for complete search history.

(56) References Cited

U.S. PATENT DOCUMENTS

| | | |
|---|---|---|
| 3,840,008 A | 10/1974 | Noiles |
| 4,139,009 A | 2/1979 | Alvarez |
| 4,326,519 A | 4/1982 | D'Alo et al. |
| 4,725,267 A | 2/1988 | Vaillancourt |
| 4,735,618 A | 4/1988 | Hagen |
| 4,790,828 A | 12/1988 | Dombrowski et al. |
| 4,867,172 A | 9/1989 | Haber et al. |
| 4,867,746 A | 9/1989 | Dufresne |
| 4,887,998 A | 12/1989 | Martin et al. |
| 4,892,521 A | 1/1990 | Laico et al. |
| 4,909,794 A | 3/1990 | Haber et al. |
| 4,911,694 A | 3/1990 | Dolan |
| 4,944,731 A * | 7/1990 | Cole ................ A61M 5/3216 604/192 |

(Continued)

FOREIGN PATENT DOCUMENTS

| | | |
|---|---|---|
| EP | 0034879 A1 | 9/1981 |
| EP | 0680767 A1 | 11/1995 |

(Continued)

*Primary Examiner* — Laura Bouchelle
(74) *Attorney, Agent, or Firm* — The Webb Law Firm

(57) ABSTRACT

A shieldable needle device including a shield assembly having a first shield member extending from a first side of a hub and a second shield member extending from a second side of the hub, the second side being substantially opposite the first side is disclosed. The shield assembly is pivotable between an open position in which a needle cannula is exposed and the first shield member is spaced apart from the second shield member and a shield position in which the first shield member contacts the second shield member and at least a portion of the first shield member and the second shield member are disposed over the distal end of the needle cannula. In one embodiment, the hub, the first shield member, and the second shield member form an integral component.

20 Claims, 11 Drawing Sheets

(56) References Cited

U.S. PATENT DOCUMENTS

| | | |
|---|---|---|
| 4,946,446 A | 8/1990 | Vadher |
| 4,955,866 A | 9/1990 | Corey |
| 4,966,591 A | 10/1990 | Yuen |
| 4,998,922 A | 3/1991 | Kuracina et al. |
| 5,059,180 A | 10/1991 | McLees |
| 5,098,401 A | 3/1992 | De Lange |
| 5,147,319 A * | 9/1992 | Ishikawa ............ A61M 25/0637 604/174 |
| 5,176,655 A | 1/1993 | McCormick et al. |
| 5,188,611 A | 2/1993 | Orgain |
| 5,242,418 A | 9/1993 | Weinstein |
| 5,250,031 A | 10/1993 | Kaplan et al. |
| 5,256,152 A | 10/1993 | Marks |
| 5,271,070 A | 12/1993 | Truong et al. |
| 5,295,972 A | 3/1994 | Mischenko |
| 5,295,975 A | 3/1994 | Lockwood, Jr. |
| 5,312,368 A | 5/1994 | Haynes |
| 5,312,369 A | 5/1994 | Arcusin et al. |
| 5,328,483 A | 7/1994 | Jacoby |
| 5,334,155 A | 8/1994 | Sobel |
| 5,348,544 A | 9/1994 | Sweeney et al. |
| 5,423,766 A | 6/1995 | Di Cesare |
| 5,445,619 A | 8/1995 | Burns |
| 5,492,536 A | 2/1996 | Mascia |
| 5,538,508 A | 7/1996 | Steyn |
| 5,549,571 A | 8/1996 | Sak |
| 5,562,633 A | 10/1996 | Wozencroft |
| 5,584,818 A | 12/1996 | Morrison |
| 5,630,803 A | 5/1997 | Tamaro |
| 5,688,241 A | 11/1997 | Asbaghi |
| 5,713,872 A | 2/1998 | Feuerborn et al. |
| 5,716,872 A | 2/1998 | Isobe |
| 5,718,239 A | 2/1998 | Newby et al. |
| 5,735,827 A | 4/1998 | Adwers et al. |
| 5,738,665 A | 4/1998 | Caizza et al. |
| 5,755,699 A | 5/1998 | Blecher et al. |
| 5,779,679 A | 7/1998 | Shaw |
| 5,833,670 A | 11/1998 | Dillon et al. |
| 5,893,845 A | 4/1999 | Newby et al. |
| 5,951,525 A | 9/1999 | Thorne et al. |
| 5,997,679 A | 12/1999 | Wheat et al. |
| 6,090,074 A | 7/2000 | Brimhall et al. |
| 6,210,371 B1 | 4/2001 | Shaw |
| 6,224,576 B1 | 5/2001 | Thorne et al. |
| 6,254,577 B1 | 7/2001 | Huet |
| 6,261,264 B1 | 7/2001 | Tamaro |
| 6,298,541 B1 | 10/2001 | Newby et al. |
| D452,003 S | 12/2001 | Niermann |
| D452,313 S | 12/2001 | Niermann |
| D452,314 S | 12/2001 | Niermann |
| 6,375,640 B1 | 4/2002 | Teraoka |
| 6,409,706 B1 | 6/2002 | Loy |
| 6,500,155 B2 * | 12/2002 | Sasso .................... A61M 5/158 604/177 |
| 6,537,259 B1 | 3/2003 | Niermann |
| 6,616,637 B2 | 9/2003 | Alexander et al. |
| 6,682,510 B2 | 1/2004 | Niermann |
| 6,918,891 B2 | 7/2005 | Bressler et al. |
| 7,150,725 B2 | 12/2006 | Wilkinson |
| 7,361,159 B2 | 4/2008 | Fiser et al. |
| 7,867,201 B2 * | 1/2011 | Huet .................... A61M 5/158 604/162 |
| 8,133,207 B2 | 3/2012 | Wilkinson |
| 8,231,583 B2 | 7/2012 | Swenson |
| 2002/0111566 A1 * | 8/2002 | Maclean Crawford .......... A61M 25/0637 600/583 |
| 2003/0036731 A1 | 2/2003 | Wilkinson et al. |
| 2003/0135157 A1 | 7/2003 | Saulenas et al. |
| 2003/0181868 A1 | 9/2003 | Swenson |
| 2003/0181870 A1 | 9/2003 | Bressler et al. |
| 2005/0065482 A1 * | 3/2005 | Hauri ................. A61M 5/3202 604/263 |

FOREIGN PATENT DOCUMENTS

| | | |
|---|---|---|
| EP | 0713710 A1 | 5/1996 |
| EP | 1132103 A1 | 9/2001 |
| EP | 1254677 A1 | 11/2002 |
| EP | 1346738 A1 | 9/2003 |
| EP | 1369142 A1 | 12/2003 |
| EP | 1374772 A1 | 1/2004 |
| EP | 1430834 A2 | 6/2004 |
| EP | 1457228 A2 | 9/2004 |
| FR | 2618685 A1 | 2/1989 |
| GB | 2202747 A | 10/1988 |
| GB | 2301036 A | 11/1996 |
| JP | 492796 | 1/1974 |
| JP | 1268563 A | 10/1989 |
| JP | 437406 U | 3/1992 |
| JP | 4261665 A | 9/1992 |
| JP | 2002325752 A | 11/2002 |
| JP | 200352820 A | 2/2003 |
| WO | 9419036 A1 | 9/1994 |
| WO | 9915222 A1 | 4/1999 |
| WO | 03026731 A1 | 4/2003 |
| WO | 2006007556 A2 | 1/2006 |

* cited by examiner

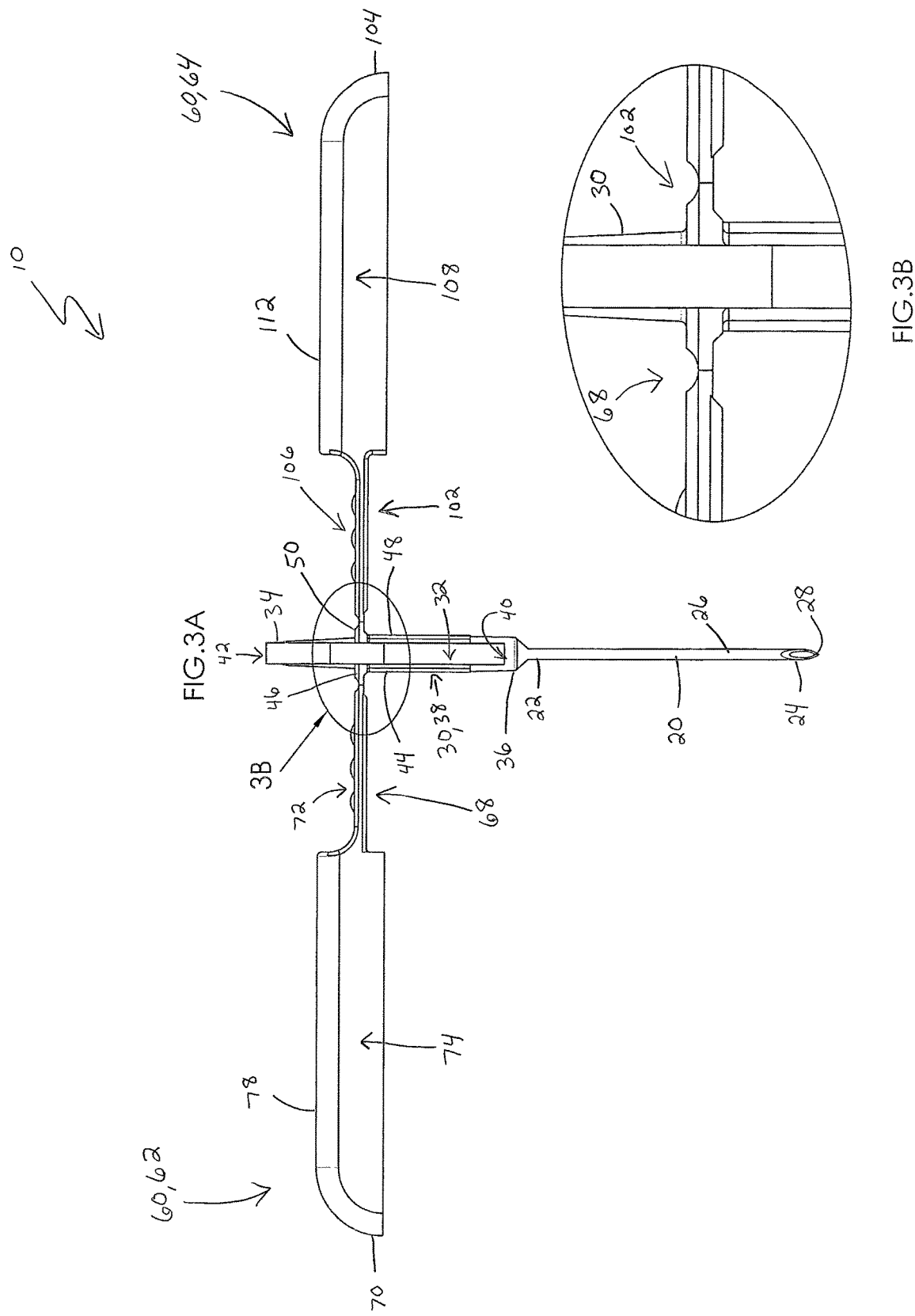

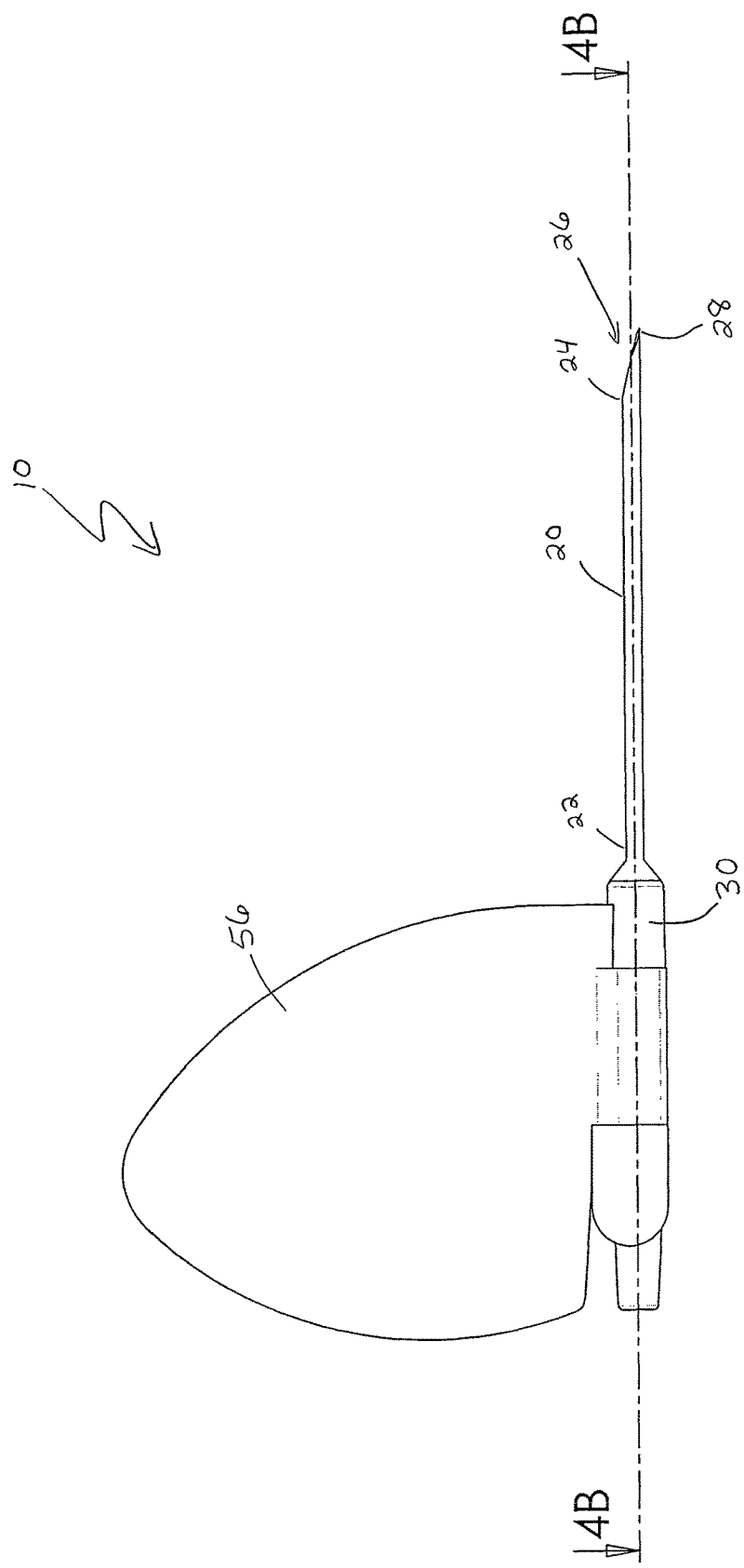

BLOOD COLLECTION DEVICE WITH DOUBLE PIVOT SHIELDS

BACKGROUND OF THE INVENTION

Field of the Invention

The present disclosure relates generally to a blood collection device for safe and convenient handling of needles. More particularly, the present disclosure relates to an inexpensive disposable blood collection device including an easily activated safety shield device for protectively shielding a pointed end of a needle assembly.

Description of Related Art

Medical devices that have piercing elements are typically used for administering a medication or withdrawing a fluid, such as blood collecting needles or fluid handling needles. Current medical practice requires that the fluid containers and needle assemblies used in such systems be inexpensive and readily disposable. Consequently, existing blood collection systems, for example, typically employ some form of a durable, reusable holder on which detachable and disposable needles and fluid collection tubes may be mounted. A blood collection system of this nature can be assembled prior to use and then disassembled after usage. Accordingly, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste.

A blood collection set or intravenous (IV) infusion set typically includes a needle cannula having a proximal end, a pointed distal end, and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube, remote from the needle cannula, may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, needle assemblies commonly employ a safety shield that can be moved into shielding engagement with a used needle cannula without risking an accidental needle stick.

SUMMARY OF THE INVENTION

The present disclosure provides a shieldable needle device including a shield assembly having a first shield member extending from a first side of a hub and a second shield member extending from a second side of the hub, the second side being substantially opposite the first side. The shield assembly is pivotable between an open position in which a needle cannula is exposed and the first shield member is spaced apart from the second shield member and a shield position in which the first shield member contacts the second shield member and at least a portion of the first shield member and the second shield member are disposed over the distal end of the needle cannula. Advantageously, by having the needle cannula, the hub, and the shield assembly form an integral component, vibration exerted upon the distal end of the needle cannula is at least partially absorbed by the integral component of the shieldable needle device. In this manner, the device of the present disclosure may provide a mechanism to at least partially absorb vibration of the needle cannula upon entering the vein of a patient during a blood collection procedure through the shieldable needle device to minimize any adverse effects of such vibration on the efficiency of the device. Additionally, the shield assembly provides a stabilizer for the needle cannula upon insertion of the distal end of the needle cannula inside a vein of a patient during a blood collection procedure. In this manner, rolling and/or undesired movement of the shieldable needle device relative to the patient is prevented.

In accordance with an embodiment of the present invention, a shieldable needle device includes a needle cannula having a proximal end and a distal end, a hub supporting at least portion of the needle cannula, and a shield assembly having a first shield member extending from a first side of the hub and a second shield member extending from a second side of the hub, the second side being substantially opposite the first side, the shield assembly pivotable between an open position in which the needle cannula is exposed and the first shield member is spaced apart from the second shield member, and a shield position in which the first shield member contacts the second shield member and at least a portion of the first shield member and the second shield member are disposed over the distal end of the needle cannula.

In one configuration, the shieldable needle device includes a dorsal fin extending from a first portion of the hub. In another configuration, the hub, the first shield member, and the second shield member form an integral component. In yet another configuration, the hub, the dorsal fin, the first shield member, and the second shield member form an integral component. In one configuration, the hub, the needle cannula, the dorsal fin, the first shield member, and the second shield member form an integral component. In another configuration, vibration exerted upon the distal end of the needle cannula is at least partially absorbed by the integral component of the shieldable needle device. In yet another configuration, the shield assembly includes a needle locking assembly for locking the shield assembly to the needle cannula when the shield assembly is in the shield position. In one configuration, the needle locking assembly includes at least one locking clip. In another configuration, the shieldable needle device includes a removable cover protectively surrounding the needle cannula and engageable with a distal portion of the hub. In yet another configuration, at least one of the first shield member and the second shield member include at least one living hinge.

In accordance with another embodiment of the present invention, a shieldable needle device includes a needle cannula having a proximal end and a distal end, a hub supporting at least a portion of the needle cannula, a dorsal fin extending from a portion of the hub in a first direction, and a shield assembly having a first shield member extending from a first side of the hub in a second direction that is perpendicular to the first direction and a second shield member extending from a second side of the hub in a third direction that is perpendicular to the first direction, the second side being substantially opposite the first side, the shield assembly pivotable between an open position in which the needle cannula is exposed and the first shield member is spaced apart from the second shield member, and a shield position in which the first shield member contacts the second shield member and at least a portion of the first shield member and the second shield member are disposed over the distal end of the needle cannula.

In one configuration, the hub, the first shield member, and the second shield member form an integral component. In another configuration, the hub, the dorsal fin, the first shield member, and the second shield member form an integral component. In one configuration, the hub, the needle cannula, the dorsal fin, the first shield member, and the second shield member form an integral component. In another configuration, vibration exerted upon the distal end of the needle cannula is at least partially absorbed by the integral component of the shieldable needle device. In yet another configuration, the shield assembly includes a needle locking assembly for locking the shield assembly to the needle cannula when the shield assembly is in the shield position. In one configuration, the needle locking assembly includes at least one locking clip. In another configuration, the shieldable needle device includes a removable cover protectively surrounding the needle cannula and engageable with a distal portion of the hub. In yet another configuration, at least one of the first shield member and the second shield member include at least one living hinge.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

FIG. 3A is a plan view of the shieldable needle device of FIG. 2 with the device in an open position in accordance with an embodiment of the present invention.

FIG. 3B is an enlarged partial cross-sectional view of the shieldable needle device of FIG. 3A taken along section 3B in accordance with an embodiment of the present invention.

FIG. 4A is a side elevation view of the shieldable needle device of FIG. 2 in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

Figure 1:
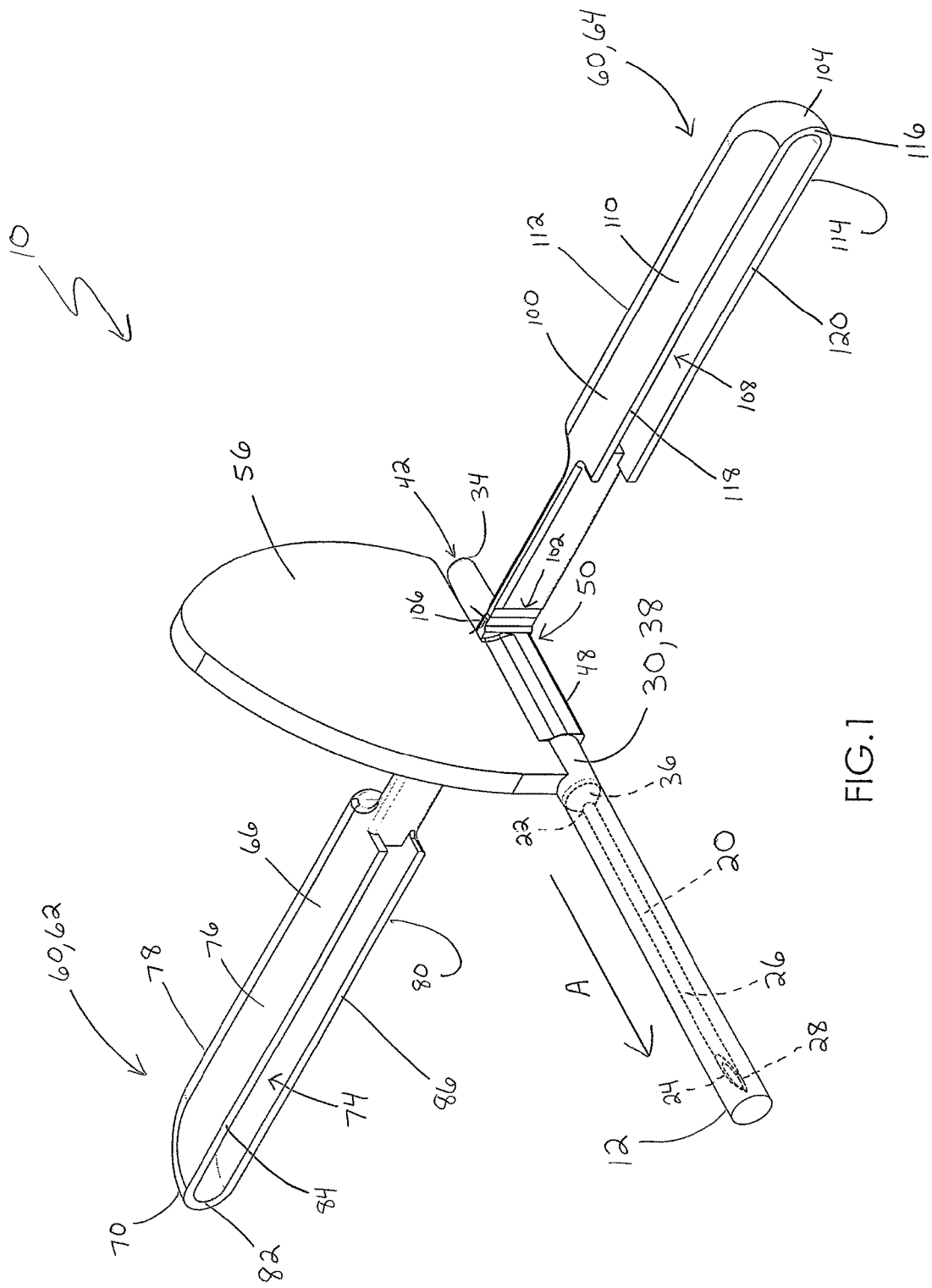
FIG. 1 is an assembled, perspective view of a shieldable needle device with a protective cover in accordance with an embodiment of the present invention.
Figure 2:
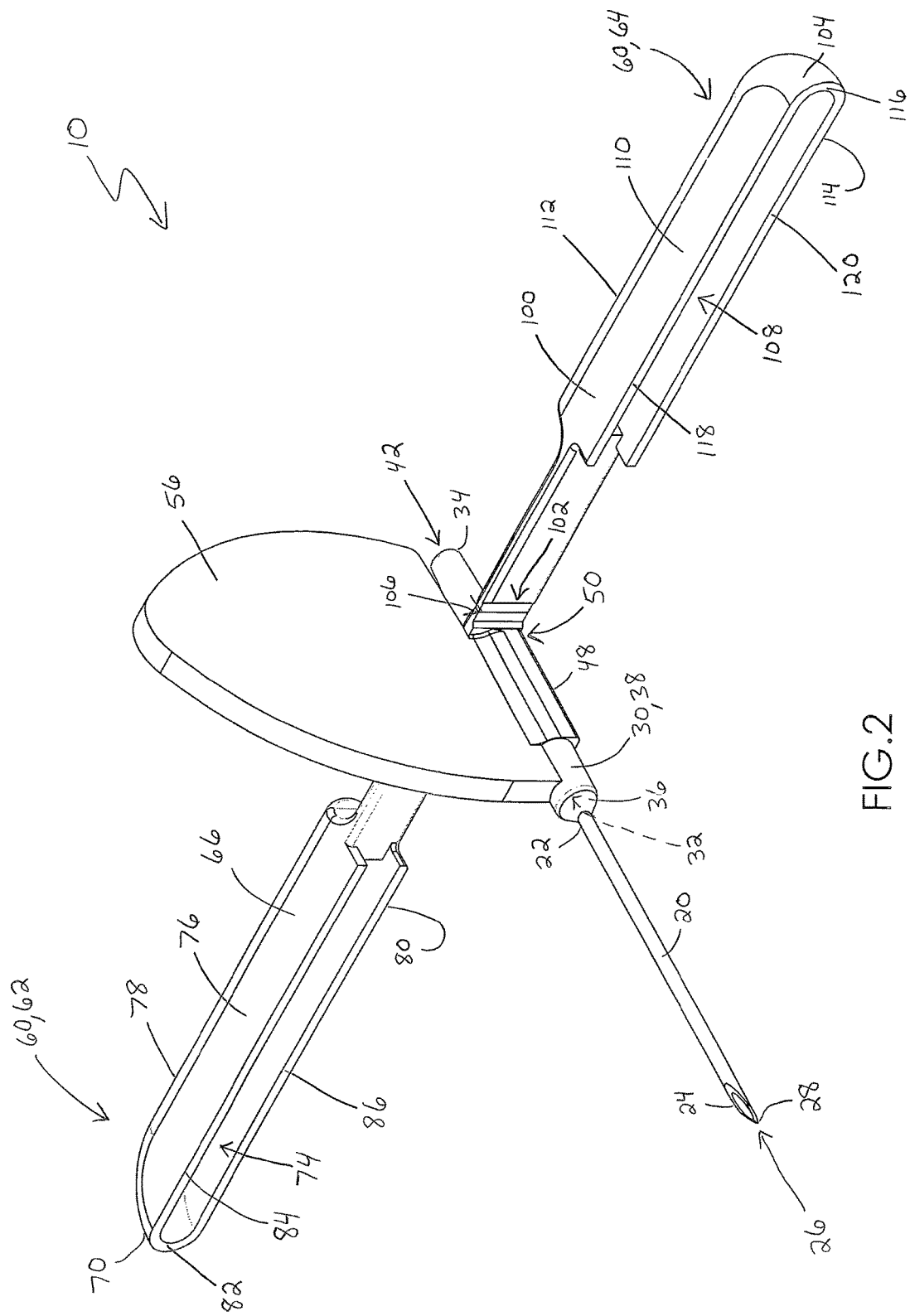
FIG. 2 is a perspective view of the shieldable needle device of FIG. 1 with the protective cover removed in accordance with an embodiment of the present invention.
Figure 4B:
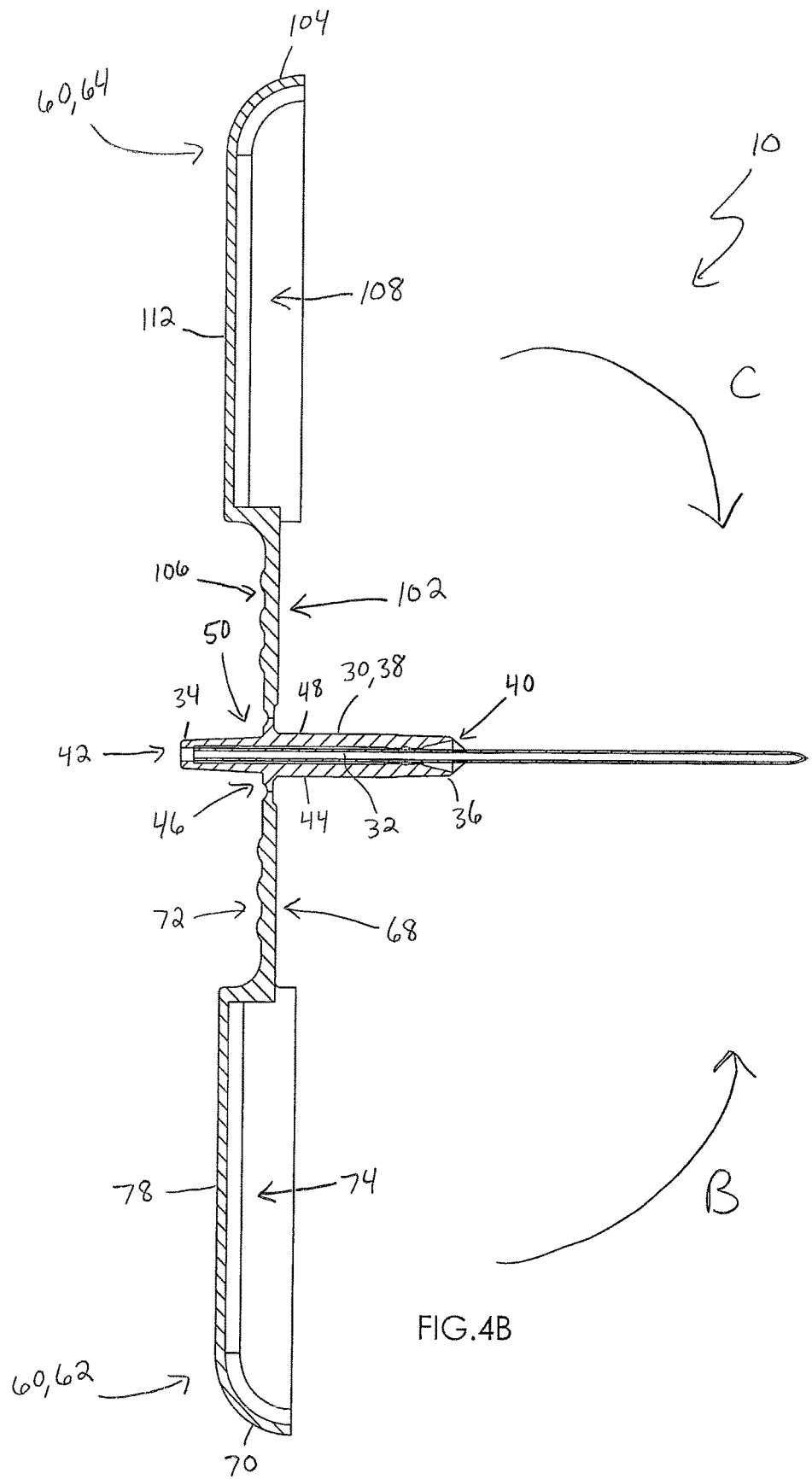
FIG. 4B is a plan cross-sectional view taken along line 4B-4B of the shieldable needle device of FIG. 4A in accordance with an embodiment of the present invention.
Figure 5:
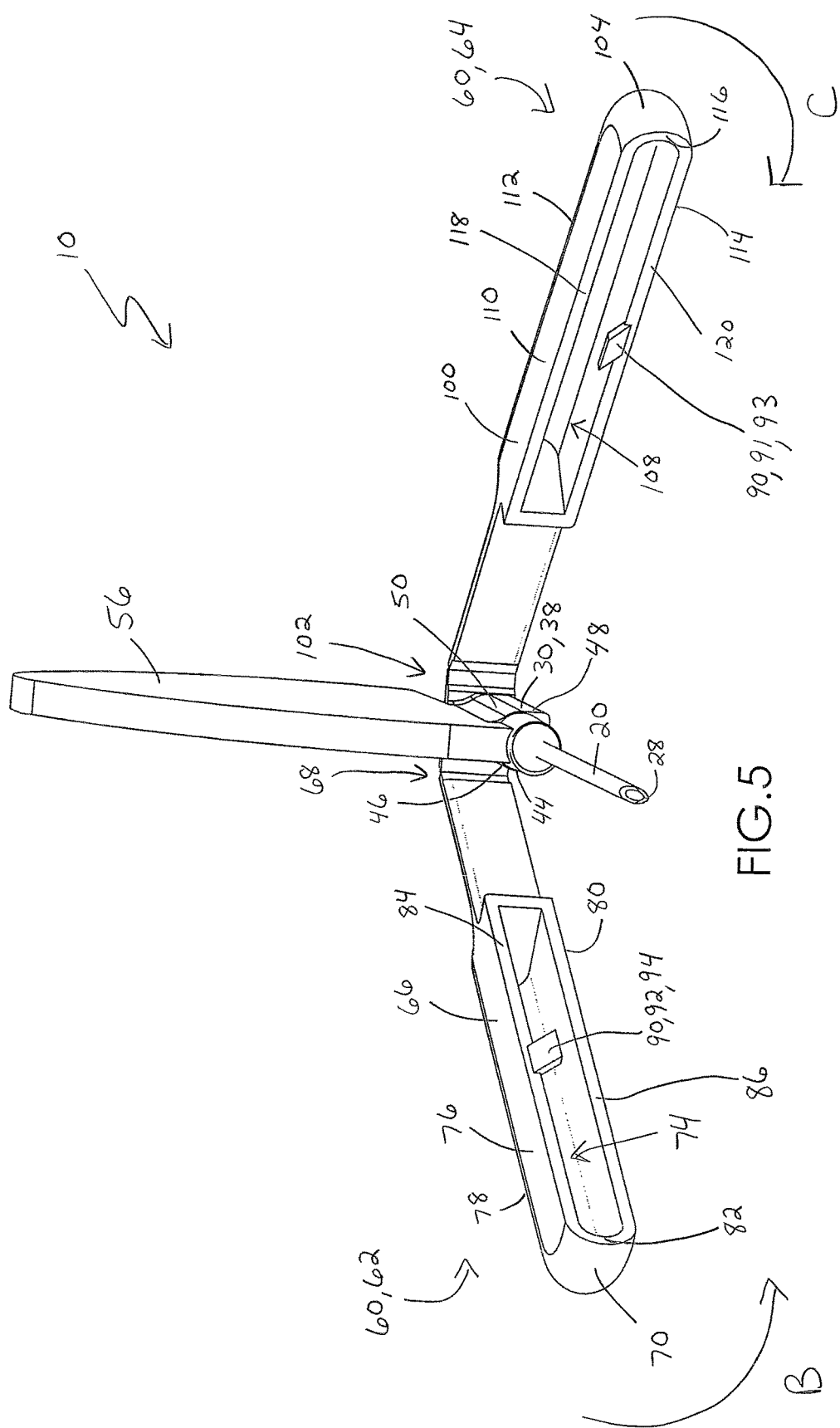
FIG. 5 is a perspective view of the shieldable needle device of FIG. 2 in a partially open position in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a needle assembly adapted for contact with a patient, and "proximal" refers to the opposite direction of distal, i.e., away from the end of a needle assembly adapted for contact with a patient. For purposes of this disclosure, the above-mentioned references are used in the description of the components of a shieldable needle device in accordance with the present disclosure.

Referring to FIGS. 1-8, a shieldable needle device 10 includes a packaging cover 12 (FIG. 1), a needle cannula 20, a hub 30, a dorsal fin 56, a shield assembly 60, and a needle locking assembly 90 as will be described in more detail below. In one embodiment, packaging cover 12 is removably mounted to hub 30 such that cover 12 protectively surrounds needle cannula 20 as shown in FIG. 1. In one embodiment, cover 12 may be removably mounted to shieldable needle device 10 through a frictional engagement, interference fit, or similar securement method.

Referring to FIGS. 1-8, needle cannula 20 includes a proximal end 22 and an opposing distal end 24, with a lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Figure 6:
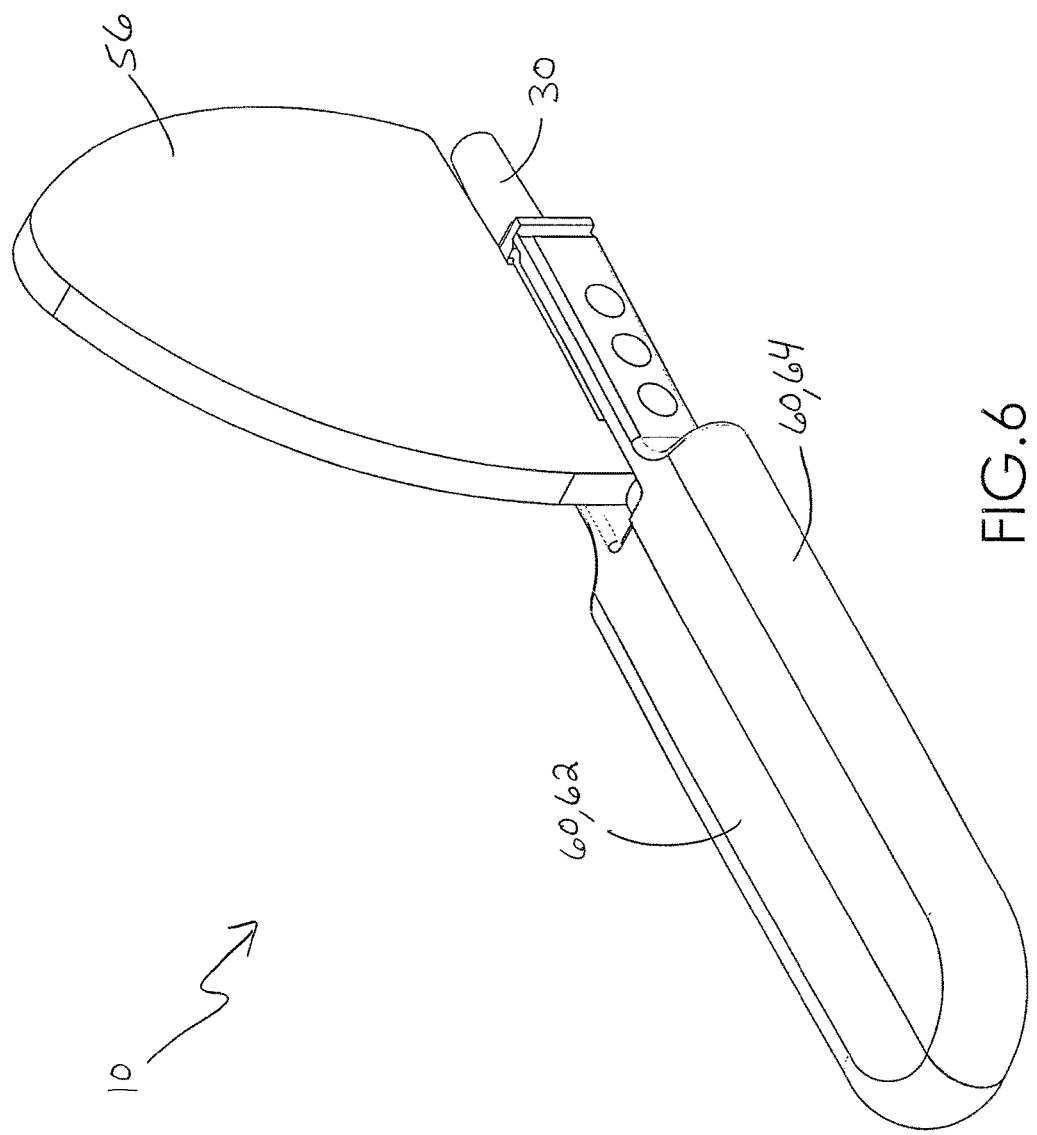
FIG. 6 is a perspective view of the shieldable needle device of FIG. 2 in a shield position in accordance with an embodiment of the present invention.
Figure 7:
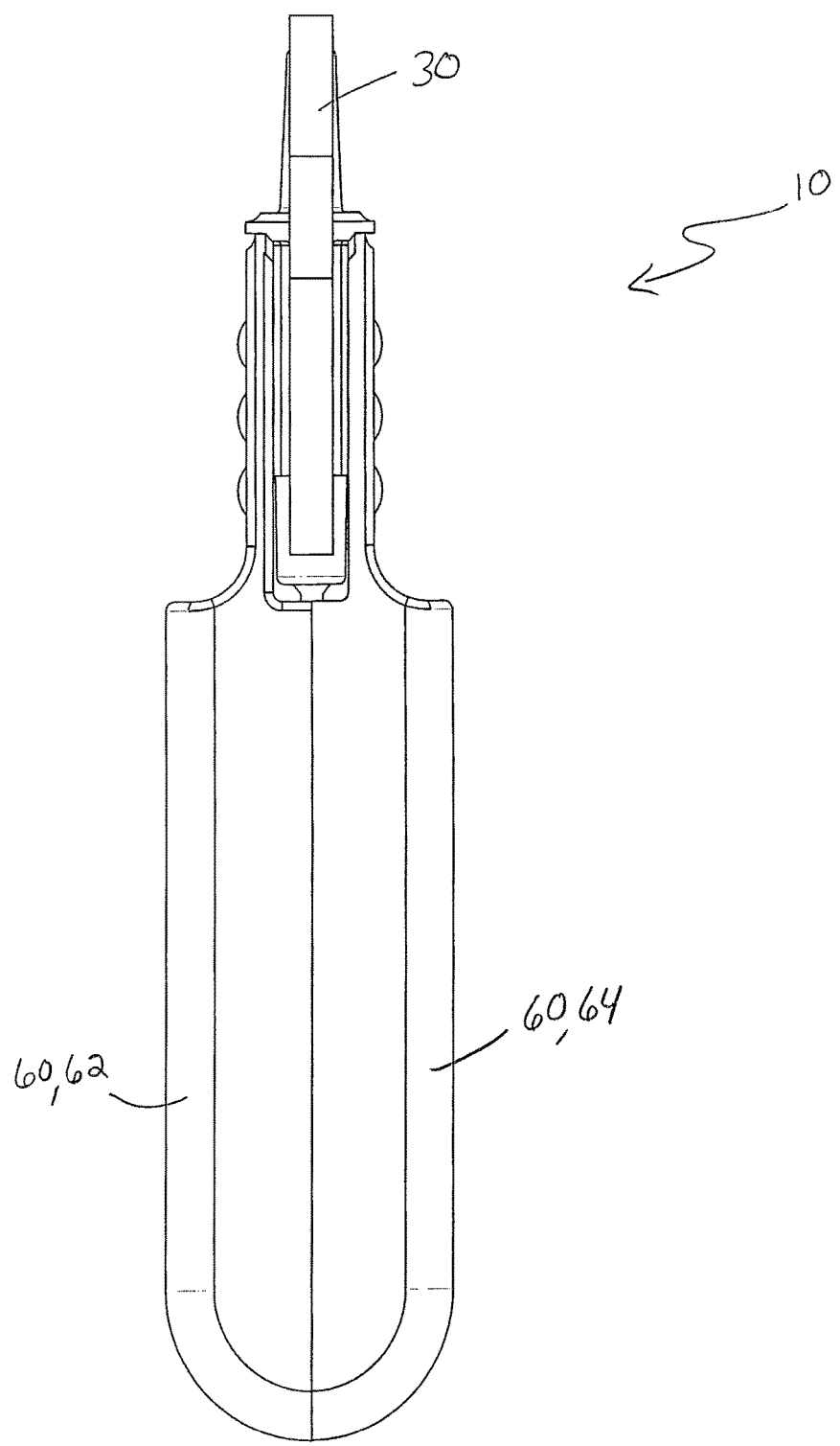
FIG. 7 is a plan view of the shieldable needle device of FIG. 6 in the shield position in accordance with an embodiment of the present invention.
Figure 8:
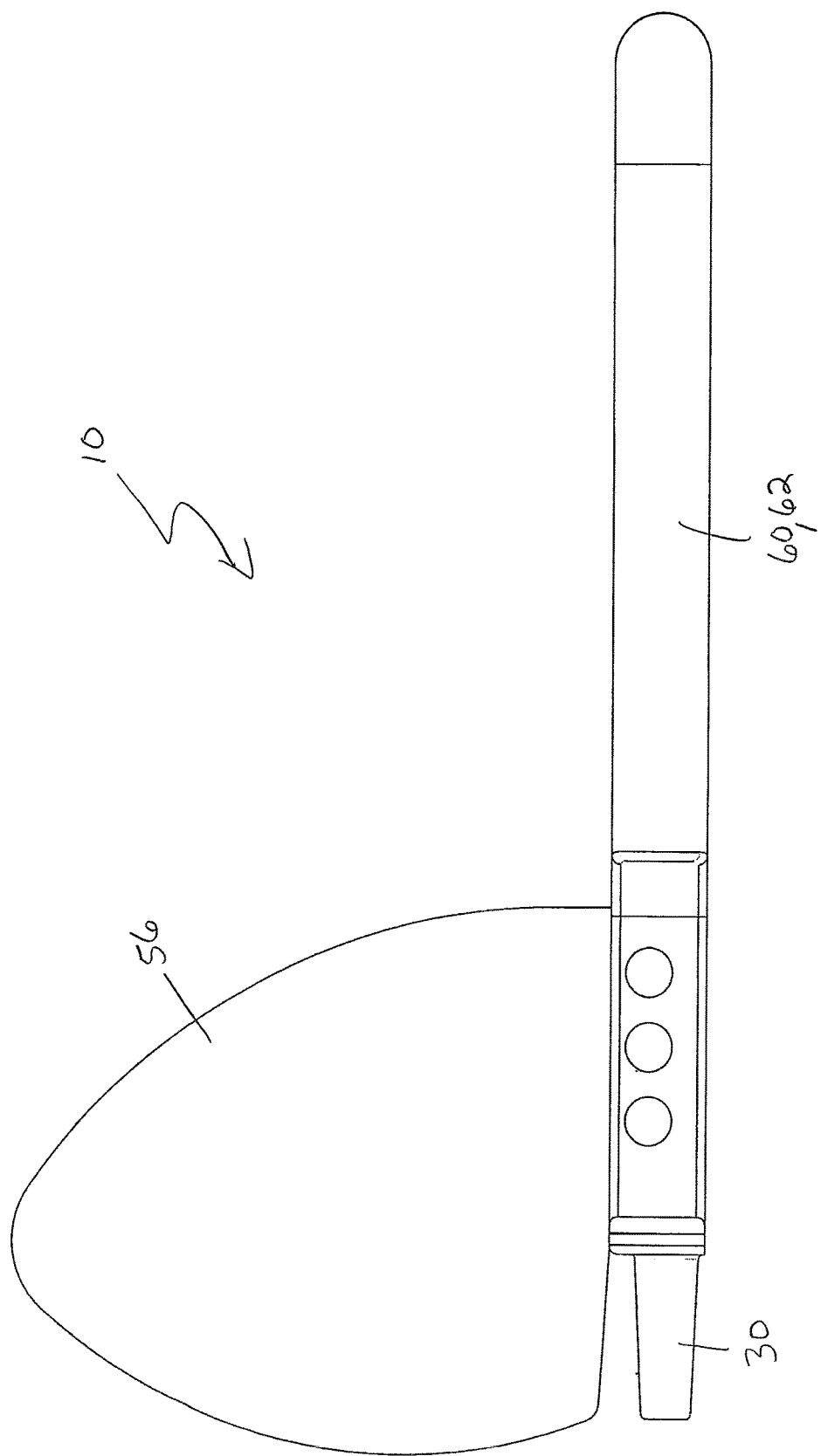
FIG. 8 is a side elevation view of the shieldable needle device of FIG. 6 in the shield position in accordance with an embodiment of the present invention.

Referring to FIGS. 1-8, shieldable needle device 10 includes hub 30. In one embodiment, hub 30 is a unitary structure, desirably molded from a thermoplastic material. In another embodiment, hub 30 may be integrally formed with dorsal fin 56 as discussed below. In another embodiment, hub 30 may be integrally formed with shield assembly 60 as discussed below. In such an embodiment, the integral component of hub 30 and shield assembly 60 forms a retainer member that supports proximal end 22 of needle cannula 20 and that is movable or pivotable between an open position (FIGS. 1-4B) and a shield position (FIGS. 6-8). Advantageously, the design of the shieldable needle device 10 of the present disclosure allows for an integrally formed component. In this manner, device 10 may provide a mechanism to at least partially absorb vibration of needle cannula 20 upon entering the vein of a patient during a blood collection procedure through device 10 to minimize any adverse effects of such vibration on the efficiency of device 10.

In one embodiment, hub 30 includes a proximal end 34, an opposing distal end 36, and a hub central passage 32 extending between proximal end 34 and distal end 36. In this manner, proximal end 34 and distal end 36 of hub 30 are in fluid communication via hub central passage 32. In one embodiment, hub 30 is defined by a rigid structure or hub structure 38 extending between proximal end 34 and distal end 36. Hub structure 38 defines a distal opening 40 at distal end 36 and a proximal opening 42 at proximal end 34. Distal opening 40 of hub 30 is adapted to receive proximal end 22 of needle cannula 20. In this manner, hub 30 is configured to support proximal end 22 of needle cannula 20 and needle cannula 20 and hub 30 are in fluid communication. For example, proximal end 22 of needle cannula 20 is securely mounted with hub 30 so that a central passage 32 of hub 30 is in fluid communication with lumen 26 of needle cannula 20. In one embodiment, needle cannula 20 can be positioned within distal opening 40 of hub 30 so that a portion of needle cannula 20 extends from distal end 36 of hub 30. In one embodiment, needle cannula 20 and hub 30 may be separate parts which are fixedly attached and secured through an appropriate medical grade adhesive, for example, epoxy or similar adhesive material. In some embodiments, needle cannula 20 and hub 30 may be fixedly attached via other mechanical mechanisms, for example, a snap-fit mechanism, an interference fit, or similar mechanisms. In another embodiment, needle cannula 20 and hub 30 may form an integral component. For example, needle cannula 20 and hub 30 may be integrally molded in a two-step molding process.

Proximal opening 42 of hub 30 is adapted to receive a flexible tube of a blood collection assembly, or other medical device, such as a tube holder or similar component. In one embodiment, a thin flexible thermoplastic tubing of a blood collection assembly may be connected to proximal opening 42 of hub 30 so that the tubing is in fluid communication with lumen 26 of needle cannula 20. For example, the flexible tubing can be mounted to proximal end 34 of hub 30 such that the passage through the tubing communicates with lumen 26 of needle cannula 20. The end of the tubing remote from needle cannula 20 may include a fixture mounted thereon for connecting needle cannula 20 to a blood collection tube or some other receptacle. For example, the fixture of a blood collection assembly may enable needle cannula 20 and the tubing to be placed in communication with an appropriate receptacle, such as a blood collection tube. The specific construction of such a fixture and blood collection assembly will depend upon the characteristics of the receptacle to which the fixture and blood collection assembly will be connected.

Shieldable needle device 10 can be packaged substantially in the condition shown in FIG. 1 in protective packaging, such as in a blister package. Prior to use, shieldable needle device 10 is removed from any protective package, and a fixture of a blood collection assembly may be connected to an appropriate receptacle for providing fluid communication with lumen 26 extending through needle cannula 20 as will described in more detail below.

Hub 30 includes structure for mating with shield assembly 60. For example, a first side surface 44 of hub 30 may include a first shield connection element 46 for connection with a first shield member 62. An opposing second side surface 48 of hub 30 may include a second shield connection element 50 for connection with a second shield member 64. In one embodiment, first shield connection element 46 and second shield connection element 50 may include snap-fit mechanisms for quick coupling of first shield member 62 and second shield member 64 to hub 30. In other embodiments, hub 30 may include different types of structures for mating with first shield member 62 and second shield member 64. In all embodiments, first shield member 62 and second shield member 64 are secured to hub 30 such that first shield member 62 and second shield member 64 are movable or pivotable relative to hub 30 so that first shield member 62 and second shield member 64 may be pivoted to protectively shield needle cannula 20 as will be described in more detail below and with reference to FIGS. 6-8.

Referring to FIGS. 1-8, shieldable needle device 10 includes dorsal fin 56. Dorsal fin 56 may extend from a surface of hub structure 38 in a first direction. Dorsal fin 56 may provide a single interface to hold and maneuver shieldable needle device 10. In one embodiment, dorsal fin 56 may include a plurality of tactile bumps to promote a gripping surface for a user of shieldable needle device 10.

Referring to FIGS. 1-8, shieldable needle device 10 includes shield assembly 60. In one embodiment, shield assembly 60 may be a unitary structure. As discussed above, in another embodiment, hub 30 and shield assembly 60 may be integrally molded in a molding process. In other embodiments, hub 30 and shield assembly 60 are separate pieces rather than being integrally molded. In one such embodiment, hub 30 and shield assembly 60 may be separate parts which are fixedly attached and secured through an appropriate medical grade adhesive, for example, epoxy or similar adhesive material. In other embodiments, hub 30 may be secured to shield assembly 60 by a snap fit mechanism, a locking tab mechanism, a spring loaded locking mechanism, a latch, or other similar mechanism.

In one embodiment, shield assembly 60 includes first shield member 62 and second shield member 64. Both shield members 62, 64 are movable or pivotable relative to hub 30 between an open position (FIGS. 1-4B) and a shield position (FIGS. 6-8) in which needle cannula 20 is protectively shielded by first shield member 62 and second shield member 64.

In one embodiment, first shield member 62 extends from first side surface 44 of hub 30 in a second direction that is perpendicular to the first direction that dorsal fin 56 extends from a surface of hub structure 38 and second shield member 64 extends from second side surface 48 of hub 30 in a third direction that is perpendicular to the first direction that dorsal fin 56 extends from a surface of hub structure 38, second side surface 48 being substantially opposite first side surface 44. In some embodiments, shield assembly 60 may be pivotable between an open position (FIGS. 1-4B) in which needle cannula 20 is exposed and first shield member 62 is spaced apart from second shield member 64, and a shield position (FIGS. 6-8) in which first shield member 62 contacts second shield member 64 and at least a portion of first shield member 62 and second shield member 64 are disposed over distal end 24 of needle cannula 20.

In one embodiment, first shield member 62 includes a body portion 66 extending between an inside or hinge portion 68 and an outside side wall 70. Body portion 66 of first shield member 62 provides a component for assisting in positioning, stabilizing, and placement of shieldable needle device 10 and a blood collection assembly during a blood collection procedure. For example, first shield member 62 may act as a stabilizer for needle cannula 20 while sharp puncture tip 28 is inside a vein of a patient during a blood collection procedure. In this manner, rolling and/or undesired movement of shieldable needle device 10 relative to the patient is prevented.

Hinge portion 68 of first shield member 62 includes structure for mating with hub 30 such that first shield member 62 is pivotable relative to hub 30 as discussed above. In one embodiment, hinge portion 68 may include a living hinge mechanism. In some embodiments, hinge portion 68 may include skive portions 72 to assist in the pivoting of first shield member 62 from the open position to the shield position. With first shield member 62 in the shield position, first shield member 62 protectively surrounds distal end 24 of needle cannula 20.

Body portion 66 of first shield member 62 defines a first needle receiving cavity 74. In one embodiment, body portion 66 includes an upper wall 76, a rearward or outside wall 78, a bottom wall 80, a front or inside wall 82, and side wall 70 which together define and protectively enclose first needle receiving cavity 74. In one embodiment, inside wall 82 includes top inside wall 84 and bottom inside wall 86. First needle receiving cavity 74 of first shield member 62 protectively surrounds distal end 24 of needle cannula 20 with first shield member 62 in the shield position as shown in FIGS. 6-8 and as will be described in further detail below.

Second shield member 64 also includes a body portion 100 extending between an inside or hinge portion 102 and an outside side wall 104. Body portion 100 of second shield member 64 provides a component for assisting in positioning, stabilizing, and placement of shieldable needle device 10 and a blood collection assembly during a blood collection procedure. For example, second shield member 64 may act as a stabilizer for needle cannula 20 while sharp puncture tip 28 is inside a vein of a patient during a blood collection procedure. In this manner, rolling and/or undesired movement of shieldable needle device 10 relative to the patient is prevented.

Hinge portion 102 of second shield member 64 includes structure for mating with hub 30 such that second shield member 64 is pivotable relative to hub 30 as discussed above. In one embodiment, hinge portion 102 may include a living hinge mechanism. In some embodiments, hinge portion 102 may include skive portions 106 to assist in the pivoting of second shield member 64 from the open position to the shield position. With second shield member 64 in the shield position, second shield member 64 protectively surrounds distal end 24 of needle cannula 20.

Body portion 100 of second shield member 64 defines a second needle receiving cavity 108. In one embodiment, body portion 100 includes an upper wall 110, a rearward or outside wall 112, a bottom wall 114, a front or inside wall 116, and side wall 104 which together define and protec-tively enclose second needle receiving cavity 108. In one embodiment, inside wall 116 includes top inside wall 118 and bottom inside wall 120. Second needle receiving cavity 108 of second shield member 64 protectively surrounds distal end 24 of needle cannula 20 with second shield member 64 in the shield position as shown in FIGS. 6-8 and as will be described in further detail below.

Figure 9:
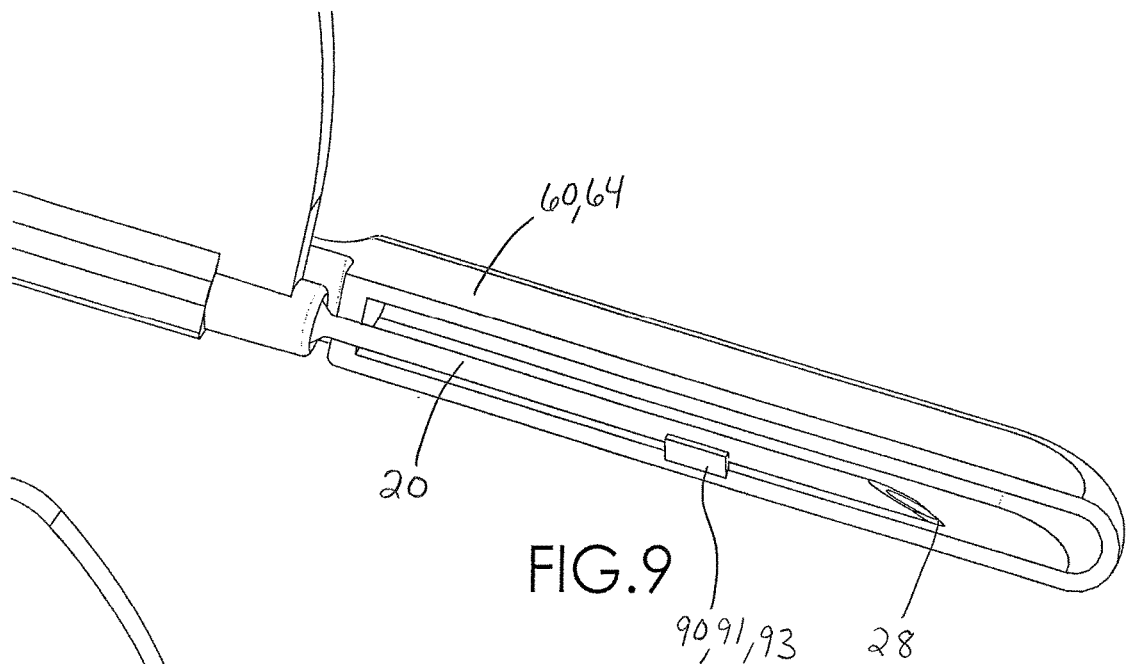
FIG. 9 is an enlarged, perspective view of a second shield locking assembly having a first locking clip in accordance with an embodiment of the present invention.
Figure 11:
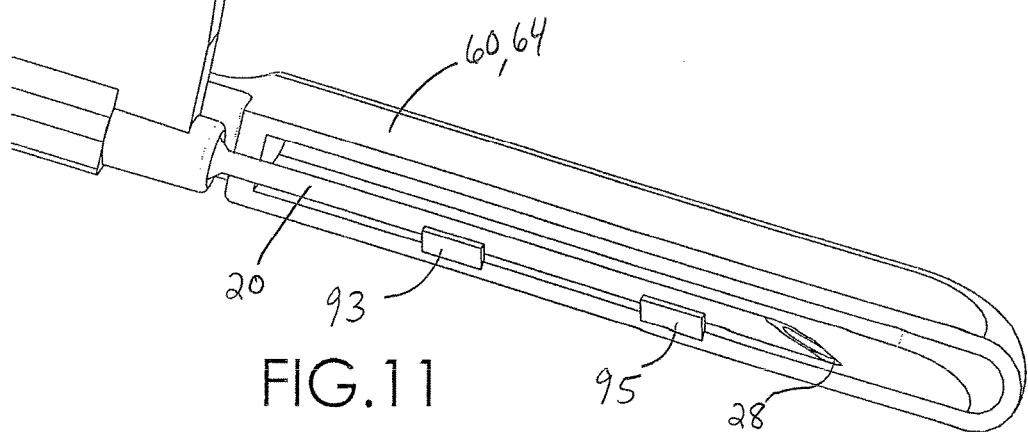
FIG. 11 is an enlarged, perspective view of a second shield locking assembly having a first and a second locking clip in accordance with an embodiment of the present invention.
Figure 10:
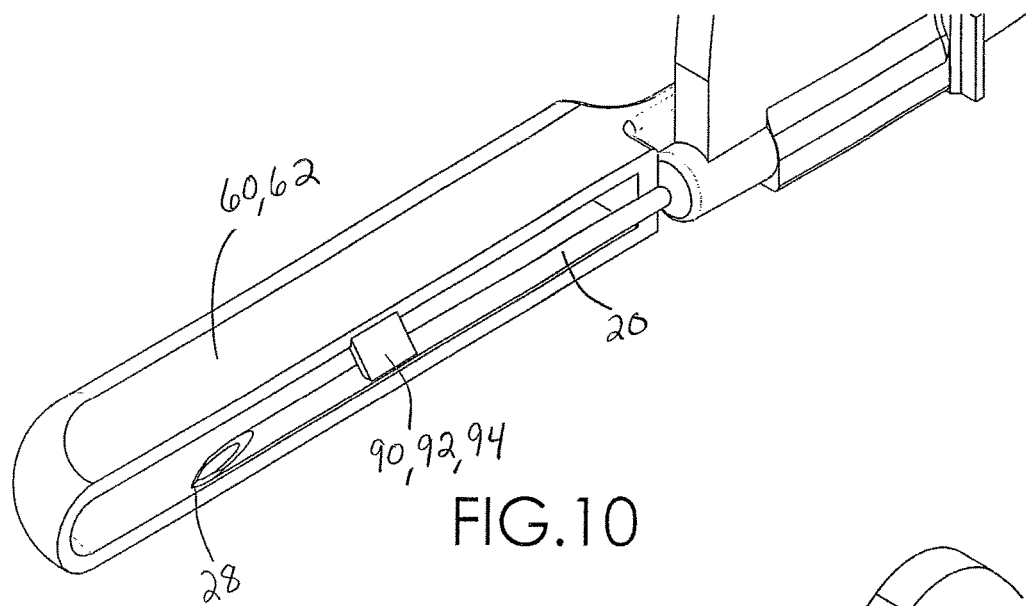
FIG. 10 is an enlarged, perspective view of a first shield locking assembly having a first locking clip in accordance with an embodiment of the present invention.
Figure 12:
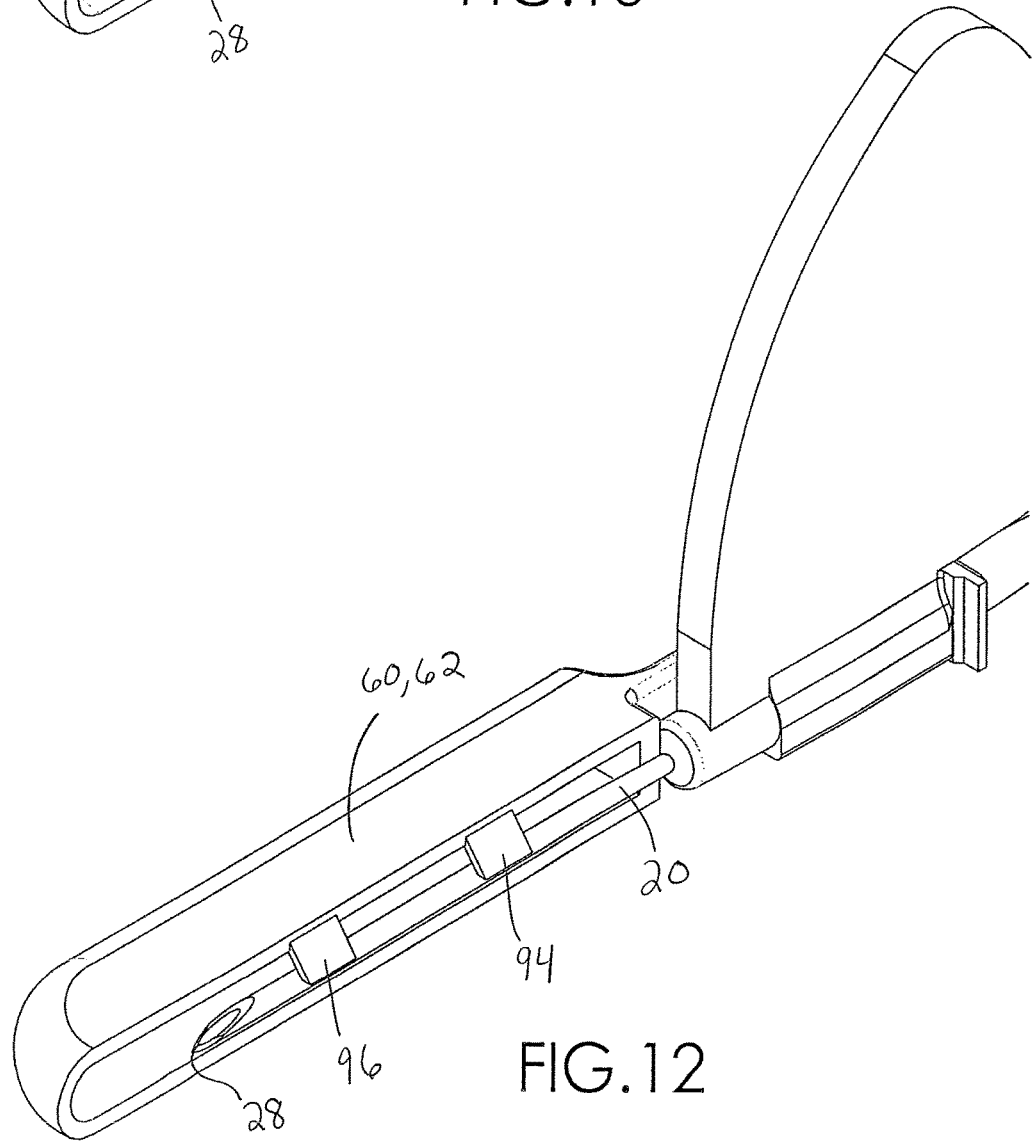
FIG. 12 is an enlarged, perspective view of a first shield locking assembly having a first and a second locking clip in accordance with an embodiment of the present invention.

Shield assembly 60 also includes needle locking assembly 90 as shown in FIGS. 9-12. Referring to FIGS. 10 and 12, first shield member 62 includes a first shield needle locking assembly 92. In one embodiment, first shield needle locking assembly 92 includes a locking clip 94 extending from top inside wall 84 as shown in FIG. 10. In another embodiment, first shield needle locking assembly 92 includes first locking clip 94 and a second locking clip 96 each extending from top inside wall 84 as shown in FIG. 12. In other embodiments, locking clip 94 could extend from top inside wall 84 and second locking clip 96 could extend from bottom inside wall 86. In other embodiments, any number of locking clips spaced from one another could be disposed along either of top inside wall 84 or bottom inside wall 86. First shield needle locking assembly 92 provides structure that locks first shield member 62 to needle cannula 20 when shield member 62 is in the shield position as will be described in more detail below.

Referring to FIGS. 9 and 11, second shield member 64 includes second shield needle locking assembly 91. In one embodiment, second shield needle locking assembly 91 includes a locking clip 93 extending from bottom inside wall 120 as shown in FIG. 9. In another embodiment, second shield needle locking assembly 91 includes first locking clip 93 and a second locking clip 95 each extending from bottom inside wall 120 as shown in FIG. 11. In other embodiments, locking clip 93 could extend from top inside wall 118 and second locking clip 95 could extend from bottom inside wall 120. In other embodiments, any number of locking clips spaced from one another could be disposed along either of top inside wall 118 or bottom inside wall 120. Second shield needle locking assembly 91 provides structure that locks second shield member 64 to needle cannula 20 when shield member 64 is in the shield position as will be described in more detail below.

As discussed above, shieldable needle device 10 can be packaged substantially in the condition shown in FIG. 1 with packaging cover 12 surrounding and protecting a sterile needle cannula 20 and in protective packaging, such as in a blister package. Prior to use, shieldable needle device 10 may be removed from any protective package, and a fixture of a blood collection assembly may be connected to an appropriate receptacle for providing fluid communication with lumen 26 extending through needle cannula 20 as discussed above.

In use, after removing shieldable needle device 10 from its protective packaging, it can be assembled with other appropriate medical equipment for use as discussed above. For example, a non-patient needle assembly and a needle holder may be connected to shieldable needle device 10 through a blood collection assembly.

To prepare for use of shieldable needle device 10, the user grasps shieldable needle device 10 at dorsal fin 56 with first shield member 62 and second shield member 64 in the open position (FIGS. 1-4B). Packaging cover 12 is then grasped and urged distally in a direction generally along arrow A (FIG. 1) to disengage cover 12 from needle cannula 20, thereby exposing puncture tip 28 of needle cannula 20.

The medical practitioner can then urge puncture tip 28 at distal end 24 of needle cannula 20 into a targeted blood vessel of a patient, while dorsal fin 56 is maintained between the thumb and forefinger of a user to assist in a controlled entry by the medical practitioner.

After the targeted blood vessel has been accessed, the medical practitioner can use first shield member 62 and second shield member 64 to assist in positioning, stabilizing, and placement of shieldable needle device 10 during the blood collection procedure. For example, first shield member 62 and second shield member 64 may act as stabilizers for needle cannula 20 while sharp puncture tip 28 is inside a vein of a patient during a blood collection procedure. In this manner, rolling and/or undesired movement of shieldable needle device 10 relative to the patient is prevented.

Upon completion of the blood collection procedure, such as when all desired samples have been drawn, needle cannula 20 is withdrawn from the patient. Upon removal of needle cannula 20 from the patient, a force may be exerted on a portion of shield assembly 60 to force first shield member 62 to pivot in a direction generally along arrow B (FIGS. 4B and 5) about hinged portion 68 to the shield position (FIGS. 6-8) in which needle cannula 20 is protectively shielded by first shield member 62. Additionally, a force may be exerted on a portion of shield assembly 60 to force second shield member 64 to pivot in a direction generally along arrow C (FIGS. 4B and 5) about hinged portion 102 to the shield position (FIGS. 6-8) in which needle cannula 20 is protectively shielded by second shield member 64.

Referring to FIGS. 9-12, as first shield member 62 and second shield member 64 are pivoted to the shield position, locking clips 93, 94, 95, 96 contact a portion of needle cannula 20 and pass distally beyond needle cannula 20. The inherent resiliency of locking clips 93, 94, 95, 96 will urge locking clips 93, 94, 95, 96 respectively over needle cannula 20 as shown in FIGS. 9-12. In this manner, a return movement of first shield member 62 and second shield member 64 to the open position is prevented. In this manner, first shield needle locking assembly 92 and second shield needle locking assembly 91 provide structure that respectively lock first shield member 62 and second shield member 64 to needle cannula 20 when shield members 62, 64 are in the shield position. This ensures that puncture tip 28 of needle cannula 20 is safely shielded. Shieldable needle device 10 may then be appropriately and safely discarded. Referring to FIGS. 6-8, with device 10 in the shield position, dorsal fin 56 can act as a handle portion during insertion, withdrawal, and disposal of shieldable needle device 10.

Advantageously, by having needle cannula 20, hub 30, dorsal fin 56, and shield assembly 60 forming an integral component, vibration exerted upon distal end 24 of needle cannula 20 is at least partially absorbed by the integral component of shieldable needle device 10. In this manner, device 10 of the present disclosure may provide a mechanism to at least partially absorb vibration of needle cannula 20 upon entering the vein of a patient during a blood collection procedure through shieldable needle device 10 to minimize any adverse effects of such vibration on the efficiency of device 10. Additionally, shield assembly 60 provides a stabilizer for needle cannula 20 upon insertion of distal end 24 of needle cannula 20 inside a vein of a patient during a blood collection procedure. In this manner, rolling and/or undesired movement of shieldable needle device 10 relative to the patient is prevented.

While the shieldable needle device of the present invention has been described in terms of one embodiment for use in connection with a blood collection system, it is further contemplated that the shieldable needle device could be used with other medical procedures, such as in conjunction with a conventional intravenous infusion set, which are well known in the art for use with needle assemblies.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A shieldable needle device comprising:
a needle cannula having a proximal end and a distal end;
a hub supporting at least a portion of the needle cannula;
a dorsal fin extending from a first portion of the hub; and
a shield assembly having a first shield member extending from a first pivot point on a first side of the hub and a second shield member extending from a second pivot point on a second side of the hub, the second side being substantially opposite the first side, wherein the first pivot point and the second pivot point are disposed proximal of a distal end of the dorsal fin, the shield assembly pivotable between an open position in which the needle cannula is exposed and the first shield member is spaced apart from the second shield member, and a shield position in which the first shield member contacts the second shield member and at least a portion of the first shield member and the second shield member are disposed over the distal end of the needle cannula,
wherein the first shield member further comprises a first body portion which, when the shield assembly is in the closed position, extends along the first side of the hub from the first pivot point to a front portion of the hub and
wherein the first side of the hub further comprises a first shield connection element for connection with the first body portion when the shield assembly is in the closed position.

2. The shieldable needle device of claim 1, wherein the hub, the first shield member, and the second shield member form an integral component.

3. The shieldable needle device of claim 1, wherein the hub, the dorsal fin, the first shield member, and the second shield member form an integral component.

4. The shieldable needle device of claim 1, wherein the hub, the needle cannula, the dorsal fin, the first shield member, and the second shield member form an integral component.

5. The shieldable needle device of claim 4, wherein vibration exerted upon the distal end of the needle cannula is at least partially absorbed by the integral component of the shieldable needle device.

6. The shieldable needle device of claim 1, wherein the needle locking assembly comprises at least one locking clip.

7. The shieldable needle device of claim 1, further comprising a removable cover protectively surrounding the needle cannula and engageable with a distal portion of the hub.

8. The shieldable needle device of claim 1, wherein at least one of the first shield member and the second shield member comprise at least one living hinge.

9. The shieldable needle device of claim 1, wherein the second shield member further comprises a second body portion which, when the shield assembly is in the closed position, extends along the second side of the hub from the second pivot point to the front portion of the hub.

10. The shieldable needle device of claim 9, wherein the second side of the hub further comprises a second shield connection element for connection with the second body portion.

11. A shieldable needle device comprising:
a needle cannula having a proximal end and a distal end;
a hub supporting at least a portion of the needle cannula;
a dorsal fin extending from a portion of the hub in a first direction; and
a shield assembly having a first shield member extending from a first pivot point on a first side of the hub in a second direction that is perpendicular to the first direction and a second shield member extending from a second pivot point on a second side of the hub in a third direction that is perpendicular to the first direction, the second side being substantially opposite the first side, wherein the first pivot point and the second pivot point are disposed proximal of a distal end of the dorsal fin, the shield assembly pivotable between an open position in which the needle cannula is exposed and the first shield member is spaced apart from the second shield member, and a shield position in which the first shield member contacts the second shield member and at least a portion of the first shield member and the second shield member are disposed over the distal end of the needle cannula,
wherein the first shield member further comprises a first body portion which, when the shield assembly is in the closed position, extends along the first side of the hub from the first pivot point to a front portion of the hub and
wherein the first side of the hub further comprises a first shield connection element for connection with the first body portion when the shield assembly is in the closed position.

12. The shieldable needle device of claim 11, wherein the second side of the hub further comprises a second shield connection element for connection with the second body portion.

13. The shieldable needle device of claim 11, wherein the hub, the first shield member, and the second shield member form an integral component.

14. The shieldable needle device of claim 11, wherein the hub, the dorsal fin, the first shield member, and the second shield member form an integral component.

15. The shieldable needle device of claim 11, wherein the hub, the needle cannula, the dorsal fin, the first shield member, and the second shield member form an integral component.

16. The shieldable needle device of claim 15, wherein vibration exerted upon the distal end of the needle cannula is at least partially absorbed by the integral component of the shieldable needle device.

17. The shieldable needle device of claim 11, wherein the needle locking assembly comprises at least one locking clip.

18. The shieldable needle device of claim 11, further comprising a removable cover protectively surrounding the needle cannula and engageable with a distal portion of the hub.

19. The shieldable needle device of claim 11, wherein at least one of the first shield member and the second shield member comprise at least one living hinge.

20. The shieldable needle device of claim 11, wherein the second shield member further comprises a second body portion which, when the shield assembly is in the closed position, extends along the second side of the hub from the second pivot point to the front portion of the hub.

* * * * *